United States Patent [19]

Kim et al.

[11] Patent Number: 5,182,373
[45] Date of Patent: Jan. 26, 1993

[54] QUATERNARY AMMONIUM-SUBSTITUTED SAPONIN ETHERS

[75] Inventors: Young D. Kim; Byung J. Ha, both of Seoul, Rep. of Korea

[73] Assignee: Pacific Chemical Co., Ltd., Seoul, Rep. of Korea

[21] Appl. No.: 530,400

[22] Filed: May 30, 1990

[30] Foreign Application Priority Data

Jun. 13, 1989 [KR] Rep. of Korea ............... 1989-8129

[51] Int. Cl.$^5$ .................... C07G 3/00; C07H 15/04
[52] U.S. Cl. .................... 536/4.1; 536/16.8
[58] Field of Search .................... 536/4.1, 16.8

[56] References Cited

U.S. PATENT DOCUMENTS

| | | | |
|---|---|---|---|
| 2,995,513 | 8/1961 | Paschall et al. | 210/731 |
| 3,532,751 | 10/1970 | Langher et al. | 536/50 |
| 4,281,109 | 7/1981 | Jarowenko et al. | 536/50 |
| 4,632,984 | 12/1986 | Matsunaga et al. | 536/50 |
| 4,663,159 | 5/1987 | Brode, II et al. | 536/43 |

OTHER PUBLICATIONS

"Organic Chemistry" Allinger et al. published 1973 pp. 458–459.

*Primary Examiner*—Nathan M. Nutter
*Assistant Examiner*—Jeffrey Culpeper Mullis
*Attorney, Agent, or Firm*—Nixon & Vanderhye

[57] ABSTRACT

The present invention provides quaternary ammonium-substituted saponin ethers having improved electrostatic and hydrophobic interactive activities, and therefore very useful in hair-care and skin-care products. The product of the invention, particularly, eliminates efficiently the static flyaway of hair and gives excellent conditioning effect to hair when used in hair-care products. The quaternary ammonium-substituted saponin ethers can be prepared by reacting a soya or ginseng saponin or an aglycone thereof with a cationic compound selected from quaternary ammonium halohydrin or quaternary ammonium epoxide.

6 Claims, 5 Drawing Sheets

FIG. 1

△ : QUATERNARY AMMONIUM-SUBSTITUTED AGLYCONE SAPONIN ETHER
○ : CETYLTRIMETHYL AMMONIUM CHLORIDE
● : SAPONIN
□ : STEARYLTRIMETHYL AMMONIUM HYDROLYSED ANIMAL PROTEIN
■ : VIRGIN HAIR (NO TREATMENT)

FIG. 2

△ : QUATERNARY AMMONIUM-SUBSTITUTED AGLYCONE SAPONIN ETHER
○ : CETYLTRIMETHYL AMMONIUM CHLORIDE
● : SAPONIN
□ : STEARYLTRIMETHYL AMMONIUM HYDROLYSED ANIMAL PROTEIN
▲ : BLEACHED (FOR 1 HOUR) HAIR (NO TREATMENT)

FIG. 3

△ : QUATERNARY AMMONIUM-SUBSTITUTED AGLYCONE SAPONIN ETHER
○ : CETYLTRIMETHYL AMMONIUM CHLORIDE
● : SAPONIN
□ : STEARYLTRIMETHYL AMMONIUM HYDROLYSED ANIMAL PROTEIN
■ : VIRGIN HAIR
▲ : BLEACHED HAIR
● : GLYCERIN
+ : PROPYLENE GLYCOL

FIG. 4

× : CONTROL
○ : CETYLTRIMETHYL AMMONIUM CHLORIDE
● : STEARYLTRIMETHYL AMMONIUM HYDROLYSED ANIMAL PROTEIN
□ : QUATERNARY AMMONIUM-SUBSTITUTED AGLYCONE SAPONIN ETHER
△ : SAPONIN

FIG. 5

× : CONTROL
○ : CETYLTRIMETHYL AMMONIUM CHLORIDE
● : STEARYLTRIMETHYL AMMONIUM HYDROLYSED ANIMAL PROTEIN
□ : QUATERNARY AMMONIUM-SUBSTITUTED AGLYCONE SAPONIN ETHER
△ : SAPONIN

QUATERNARY AMMONIUM-SUBSTITUTED SAPONIN ETHERS

FIELD OF THE INVENTION

The present invention relates to a novel quaternary ammonium-substituted saponin ether.

The novel quaternary ammonium-substituted saponin ethers according to this invention of the following general formula (I):

$$R-O-Rsap-O-R' \qquad (I)$$

Wherein,

—O—Rsap—O— is a saponin or an aglycone saponin i.e., polycyclic compound of saponin; and R and R' are hydrogen or a quaternary ammonium-containing substituent attached to aglycone saponin or saponin and at least one of them is a quaternary ammonium-containing substituent of the following formula:

wherein, $(Q)^-$ is an anion of strong inorganic acid; $R_1$ is methyl; $R_2$ and $R_3$, the same or different from each other, are each alkyl or olefin group having 18 or less carbon atoms; and t is the valency of Q, may be prepared by reacting a saponin or an aglycone saponin of soybean or ginseng with a cationic compound selected from quaternary ammonium halohydrin or quaternary ammonium epoxide.

RELATED PRIOR ART

Saponin, one of glycoside compounds occurred widely in plants, is the generic name representing polycyclic compounds containing aglycone. Most of them are obtained in an amorphous powder form, and they are readily soluble in water or methanol while hardly soluble in other organic solvents. The sugar moieties thereof are principally glucose, and sometimes replaced by galactose or arabinose.

The saponin has hydrophilic sugar moieties, and thus is a non-ionic surfactant. Aglycone moiety corresponding to liphophilic part of the saponin, i.e. the remaining part of the saponin from which the sugar moieties are removed is sometimes called as also "sapogenin" and includes steroid type and triterpene type. The saponin has been employed as an emulsifier, solubilizer, bubbling agent and detergent due to their surfactantic properties [See. Chales Zviak, "The science of hair care" Marcel Dekker Inc., New York, 67–68 (1986)].

Soya and ginseng saponins, which are main component of soybean and ginseng respectively, are already well known for their efficiency when administered orally, and particularly the ginseng saponin is said to have pharmacological activities such as protein synthesis promoting activity, glycolipid metabolism promoting activity, peripheral blood flow improving activity and the like [See. Fragrance Journal No. 58, 42–43 (1983)]. It is believed that these activites mainly due to the aglycone of the saponin [See. Takaggi K., Saito H. and Nabato H., Japan J. Pharmacol., 22, 245–259 (1972); Oura H., Hiai S., Odaka Y. and Yokazwa T., J. Biochem., 77, 1057–1065 (1975)].

Furthermore, the soya and ginseng saponins are reported to have an antioxidation activity [See. SÖFW Nr. 8, 228–229 (1985)].

These saponins have high safety when employed as a component for external preparations such as cosmetics, and had been used in order to retard the aging of skin and to provide an elasticity to skin. With regard to the using of the saponin for the purpose of hair care, it has been known that, when the saponin is sorbed onto hair, it provides better tensile strength to hair, and therefore it has been used practically for hair care.

The ginseng saponin is of dammarane series and the structure thereof has been extensively studied. It was found that the ginseng saponin comprises 13 glycosides, i.e., ginsenosides $R_o$, $R_a$, $R_{b1}$, $R_{b2}$, $R_c$, $R_d$, $R_e$, $R_f$, $R_{g1}$, $R_{g2}$, $R_{g3}$, $R_{h1}$ and $R_{h2}$ and that aglycones thereof are protopanaxadiol or protopanaxatriol [See. S. Shibata, T. Ando and T. Chsawa, Chemical studies on oriental plant drugs XIV., Chem. Pharm. Bull., 14 (1966)].

20(S)-Protopanaxadiol -
$R_4$, $R_5$:glucose derivative

20(S)-Protopanaxatriol

The 20(S)-protopanaxadiol and 20(S)-protopanaxatriol are converted to panaxadiol and panaxatriol respectively, by hydrolysis, particularly using acid or enzyme. During the hydrolysis, the C-20 hydroxy group and C-24 double bond are linked to each other to form trimethyltetrahydropyrane ring at a position of C-17. With regard to these panaxadiol and panaxatriol, the hydroxyl group of C-12 position forms a intramolecular hydrogen bond with oxygen atom of trimethylhydropyrane ring, and therefore the reaction of that hydroxyl group occurs hardly. In case of the panaxatriol, although both hydroxyl groups of C-6 and C-3 positions have an equatorial bond, it is anticipated that the hydroxyl group of C-3 position has higher reactivity since it has less steric hindrance. Further, in case of panaxadiol and panaxatriol, the fact that the primary hydroxyl groups of C-6 positions of each sugar in the sugar moiety have less steric hindrance is predicted and the reactions mostly occur at primary hydroxyl groups of sugar located at the end of the compound.

The soya saponin of oleanane series includes soya saponins I, II and III, which may be represented by the following general formula:

(IV)

wherein $R_4$ is glycosyl group;

$R_5$ is glucosyl group or hydrogen atom; and the glucosyl groups have 2 to 3 sugars bonded thereto. As can be seen in the formula, the sugar moiety located at the end of the compound undergoes the least steric hindrance and the C-6 primary hydroxyl group, among four hydroxyl groups involved therein, reacts firstly and then the secondary hydroxyl groups may react secondly.

The extensive studies on the conditioning agents for hair obtained by introducing quaternary ammonium salts to the functional groups of the natural products have been made and some compounds are used practically; for example, Polymer-JR (CTFA name: polyquaternium-10) of Union Carbide, USA, Cosmedia qua C 261 (CTFA name: guahydroxypropyltrimethylammonium chloride) of Henkel, Germany, Crotein Q (CTFA name: stearyltrimethylammonium hydrolysed animal protein) of Croda, England.

The saponin-containing products, however, have a low substantivity to hair or skin having anionic charge under normal conditions, since the saponin has many hydroxyl groups in the sugar moieties thereof and thus is non-ionic, so that it has a low electrostatic and hydrophobic interactions with hair or skin. Consequently, their effects, particularly the electrostatic flyaway-eliminating and the conditioning effects on hair or skin are not sufficient.

SUMMARY OF THE INVENTION

Therefore, the object of the invention is to provide novel quaternary ammonium-substituted saponin ethers having improved hair-care and skin-care activities.

The quaternary ammonium-substituted saponin ethers according to the invention of the following formula (I):

R—O—Rsap—O—R' (I)

Wherein,

—O—Rsap—O— is a saponin or saponin aglycone; and

R and R' are hydrogen or a quaternary ammonium-containing substituent attached to aglycone saponin or saponin and at least one of them is a quaternary ammonium-containing substituent of the following formula:

wherein, $(Q)^-$ is an anion of strong inorganic acid; $R_1$ is methyl; $R_2$ and $R_3$, the same or different from each other, are each alkyl or olefin group having less than 18 carbon atoms; and t is the valency of Q, can be prepared by reacting a saponin or aglycone saponin of soybean or ginseng with a cationic compound selected from quaternary ammonium halohydrin and quaternary ammonium epoxide.

The quaternary ammonium-substituted saponin ethers, particularly those obtained from aglycone saponin have improved electrostatic and hydrophobic interaction activities, and therefore they are very useful in haircare and basic skin-care products.

BRIEF DESCRIPTION OF THE DRAWINGS

In FIGS. 1 and 2, the line △-△ represents the hair treated with quaternary ammonium-substituted aglycone saponin prepared in Example 1, the line O-O, ●-● and □-□ represent the hairs treated with cetyltrimethyl ammonium chloride, ginseng saponin, stearyltrimethyl ammonium hydrolyzed animal protein, respectively, and the line ■-■ represents the virgin hair;

In FIG. 3, the lines O-O, X-X, △-△, □-□, O-O, ■-■, ●-●, and ▲-▲ represent gylcerin, propylene, glycol, quaternary ammonium-substituted aglycone saponin ether (Example 1), stearyltrimethyl ammonium hydrolyzed animal protein, cetyltrimethyl ammonium chloride, virgin hair, ginseng saponin and bleached hair, respectively;

In FIGS. 4 and 5, the lines O-O, □-□, ●-● and △-△ represent the hair treated with cetyltrimethyl ammonium chloride, stearyltrimethyl ammonium hydrolyzed animal protein, ginseng saponin and quaternary ammonium-substituted aglycone saponin ether (Example 1), respectively. The line X ... X represents the control.

DETAILED DESCRIPTION OF THE INVENTION

Skin and hair have an overall negative charge at normal pH due to their isoelectric point below pH 7, and they are ideal for electrostatic and hydrophobic interactions with cationic quaternary ammoniums.

The quaternary ammonium-substituted saponin ethers can maintain their cationic properties even in an alkaline solutions while primary or secondary ammonium does not. The quaternary ammonium-substituted saponin ethers have several times substantivity to hair or skin than saponin itself has. When they are used as ingredients for hair care products, they improve the easiness to comb of wet hair as well as the texture of dry hair, eliminate static flyaway of hair and increase the hydrophilic nature of hair.

The quaternary ammonium-substituted saponin ethers according to this invention can be prepared by reacting quaternary ammonium halohydrin or quaternary ammonium epoxide with saponin or aglycone saponin.

The process for preparing quaternary ammonium-substituted saponin ethers according to this invention comprises two steps:

The first step is the production of the cationic compound containing quaternary ammonium group, and the second step is the transfer of the cationic ammonium group from said cationic compound to hydroxyl group of saponin or aglycone saponin by a reaction therebetween.

The cationic compound employed in the invention is known and may be prepared by known methods.

In this invention, the cationic compound obtained in the first step is quaternary ammonium halohydrin or quaternary ammonium epoxide of the following formula:

wherein, $R_1$, $R_2$, $R_3$, $(Q)^-$ and t have the same meanings as above, and Hal is a leaving group, particularly chlorine, bromine or iodine. The quaternary ammonium halohydrin or epoxide can be prepared by a known method [e.g., U.S. Pat. No. 2,995,513] which comprises reacting a strong inorganic acid addition salt of tertiary amine with epichlorohydrin according to the following reaction scheme:

wherein, $R_1$, $R_2$, $R_3$, $(Q)^-$, t and Hal have the same meanings as above.

Suitable salts of tertiary amine employed include triethylamine hydrochloride, dimethylcyclohexylamine hydrochloride, dimethyllaurylamine hydrochloride, dimethylcetylamine hydrochloride, dimethylhexylamine hydrochloride, dipentylmethylamine hydrochloride, dimethyloleylamine hydrochloride, dimethyltalloamine hydrochloride, methyldicocoamine hydrochloride and the like. The tertiary amine salt reacts with epichlorohydrin at a range of temperature between about 10° and 100° C. to form quaternary ammonium halohydrin. Thus obtained quaternary ammonium halohydrin can be purified by recrystallization using a suitable alcohol such as ethanol or isopropanol.

The quaternary ammonium halohydrin was reacted with an equimolar amount of strong base such as sodium hydroxide or potassium hydroxide to prepare quaternary ammonium epoxide. The reaction temperature was 0° C. to 75° C., preferably 5° to 60° C.

The saponin may be used as itself or as a form of solution or dispersion of aglycone saponin. The solution or dispersion of aglycone saponin can be prepared by removing the sugar moieties from the saponin with an acid or an enzyme, e.g., glucosidase and dissolving or dispersing it in water or an inert solvent such as acetonitrile, lower branched alcohol, acetone or dioxane. As a lower branched alcohol, those one having 2 to 4 carbon atoms may be advantageously employed. The reaction time for quaternization is about 0.5 to 15 hours, preferably 3 to 8 hours. An alkali catalyst, for example, sodium hydroxide, potassium hydroxide or lithium hydroxide may be employed to promote the reaction. The amount of the catalyst used varies depending on the type of quaternizing agent, quaternary ammonium halohydrin or quaternary ammonium epoxide as well as the degree of quaternization of saponin. When quaternary ammonium halohydrin is used, the amount of the catalyst is 1 to 5 moles per mole of the former. If quaternary ammonium epoxide is used, the amount of the catalyst is 0.1 to 3 moles per mole of the former. For the quaternization, about 1 to 5 moles of quaternary ammonium is required relative to one mole of saponin.

The anionic moiety of the quaternary ammonium-substituted saponin ether according to this invention is either anion attached to the quaternary ammonium compound or one which had been introduced by ion exchange reaction. Thus, it will be, for example, chloride anion if 3-chloro-2-hydroxypropyltrimethyl ammonium chloride was used for introduction of quaternary ammonium. Furthermore, it can be substituted by nitrate, sulfate or acetate by using anion exchange resin. Such an ion exchange can be achieved by titrating the solution of quaternary ammonium-substituted saponin ether with soluble silver salt or by adding an excess amount of the desired anion followed by dialysis.

The compounds of this invention may be formulated into the form of emulsion, solution or aerosol by conventional techniques in the art of cosmetics. It may be incorporated into, particularly hair-care products such as shampoo, hair rinse, hair-treatment cream, hair lotion or hair tonic; basic skin-care products such as face cream or lotion; and make-up cosmetics such as foundation or compact powder. It eliminates efficiently the static flyaway of hair and gives conditioning effect to hair when applied to hair as hair-care products. Moreover, it makes the skin moist, soften and elastic due to its good sorption onto skin as well as its excellent moisture retention effect when applied to skin as basic skin-care products.

The properties of moisture retention effect, tensile strength for 20% extension and eye irritation of quaternary ammonium-substituted saponin ethers according to this invention were evaluated. Furthermore, half-head test of the present compound-containing shampoo was carried out to evaluate the hair-conditioning effects of the present compound.

Experimental Example 1. Moisture retention effect

Moisture retention effects on virgin and bleached hair were evaluated by measuring the moisture absorption regain(%) of quaternary ammonium-substituted saponin ether of this invention, ginseng saponin, stearyltrimethylammonium hydrolysed animal protein or cetyltrimethylammonium chloride as commercial standards, and propylene glycol or glycerin.

The moisture absorption regain(%) test was effected as follows: two grams of the virgin and bleached hair tresses were prepared and conditioned at 20% relative humidities. After that, the equilibrium weight of the tresses were measured. Then, the tresses were treated with 50 ml solutions of 0.5% test material at 20°±2° C. for 15 hours, rinsed with 50 ml distilled water twice and finally conditioned at given relative humidities (20-95%) for 10 hours at 20°±2° C. Measurements of the weight of the hair tresses at given conditions were carried out on an electrobalance to 0.1 mg accuracy in humidity controlled room at 20° C. Under the same conditions, moisture retention effect of quaternary ammonium-substituted saponin ether itself was also compared with that of commercial standard, and of propylene glycol or glycerin which is one of the most useful humectants in cosmetics.

$$\text{Moisture absorption regain}(\%) = \frac{W_1 - W_0}{W_0} \times 100$$

where $W_0$ is the weight at initial conditions (20±4% RH, 20°±2° C.) and $W_1$ is the weight at given conditions.

Figure 1:
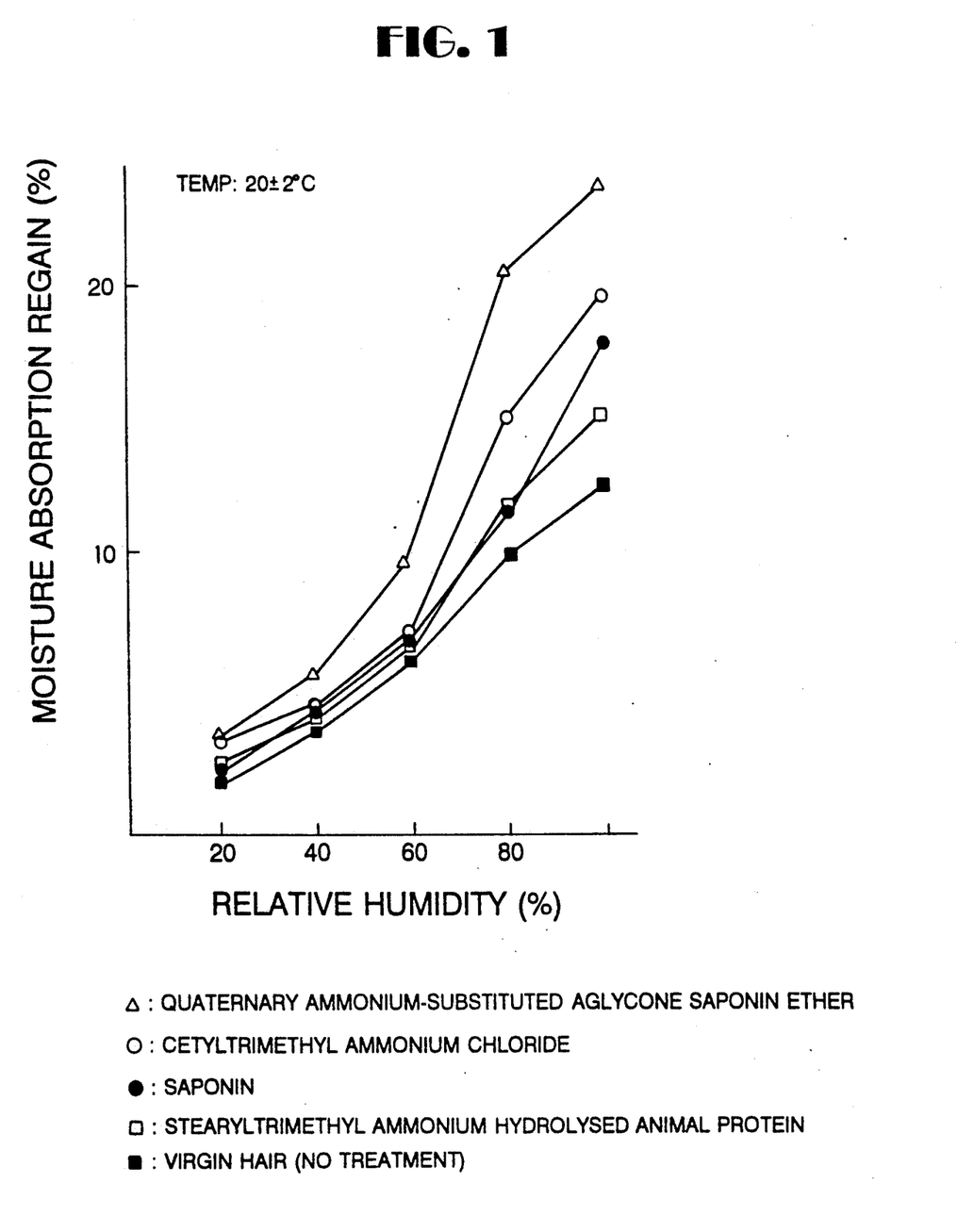
FIGS. 1 and 2 are the moisture absorption regain isotherms of virgin and bleached hair respectively, treated with quaternary ammonium-substituted aglycone saponin ether of the invention and other compounds according to Experimental Example 1.
Figure 2:
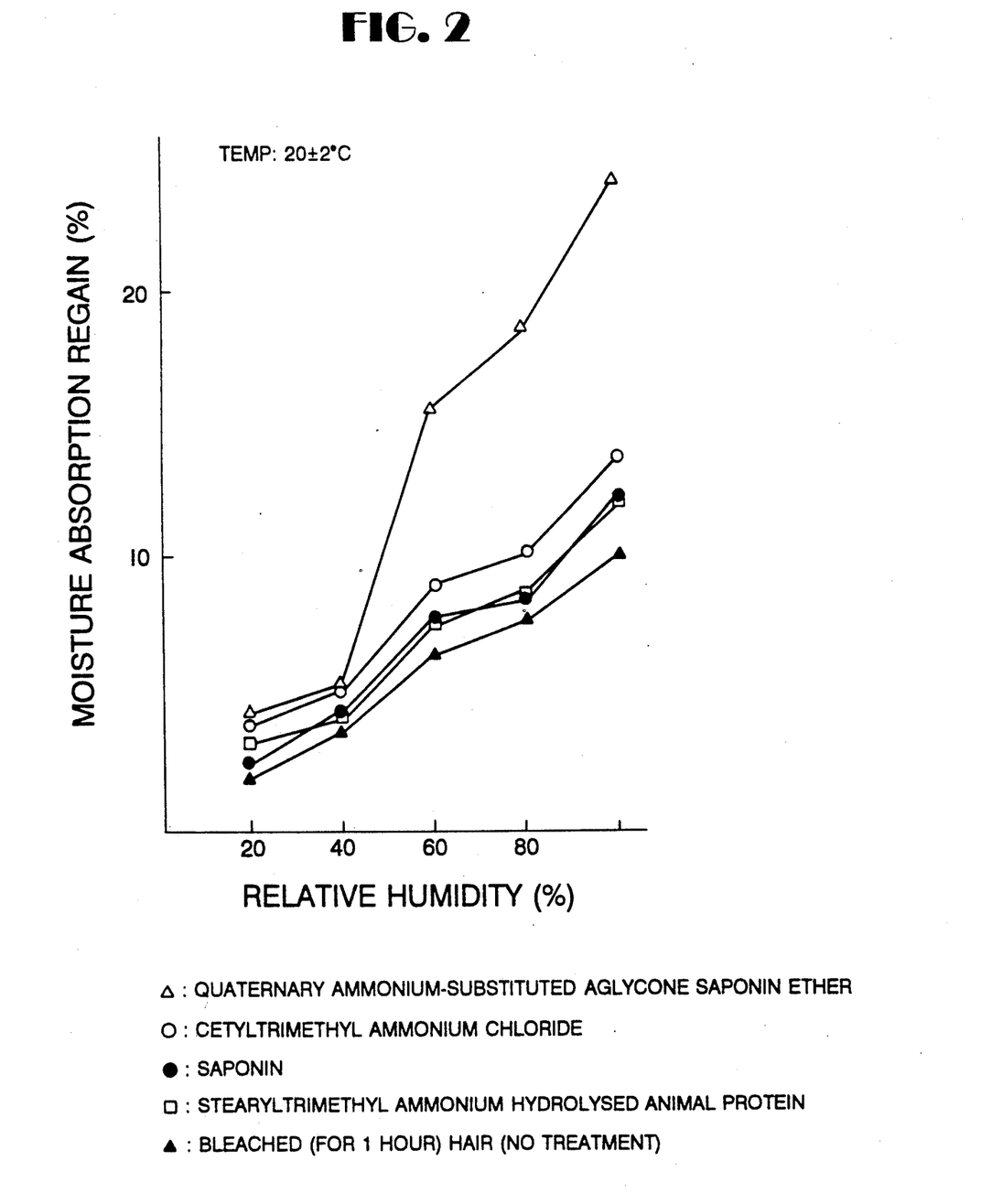
Figure 3:
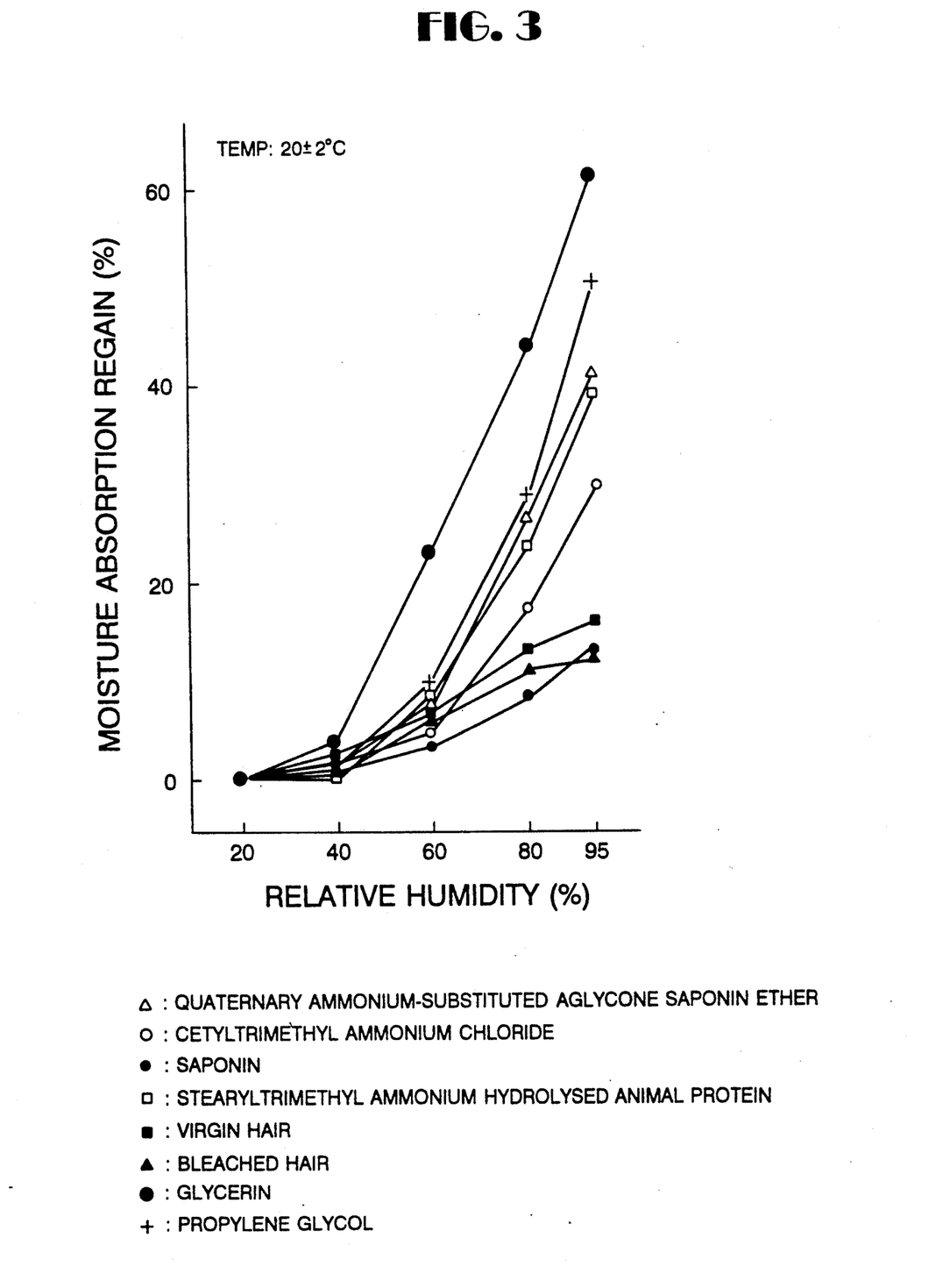
FIG. 3 is the moisture absorption regain isoltherms of various materials according to Experimental Example 1.
Figure 4:
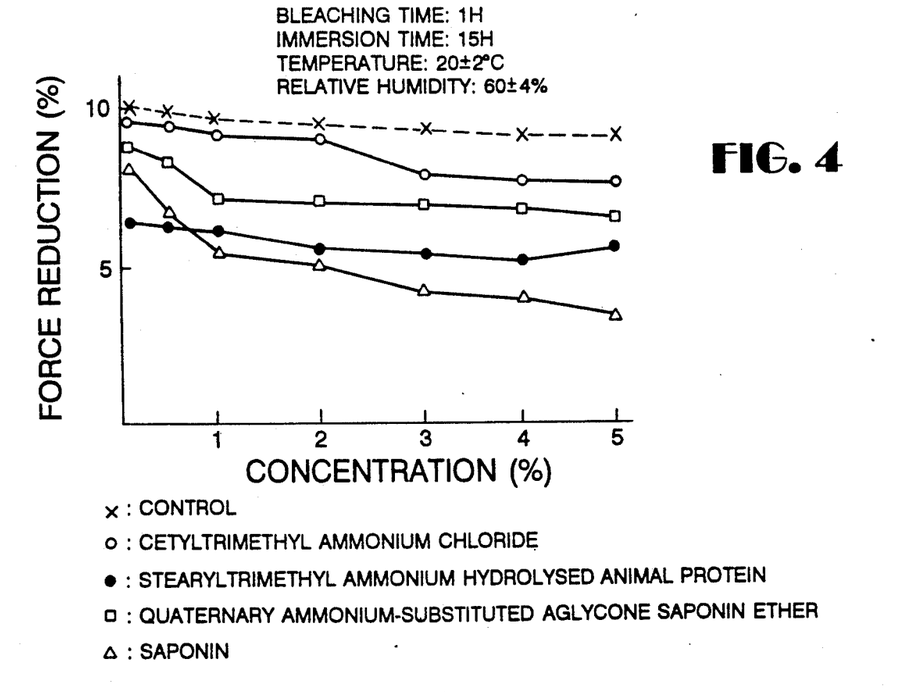
FIGS. 4 and 5 show the effects of concentration and immersion time of the test materials respectively, on force reduction (%) of bleached hair according to Experimental Example 2.
Figure 5:
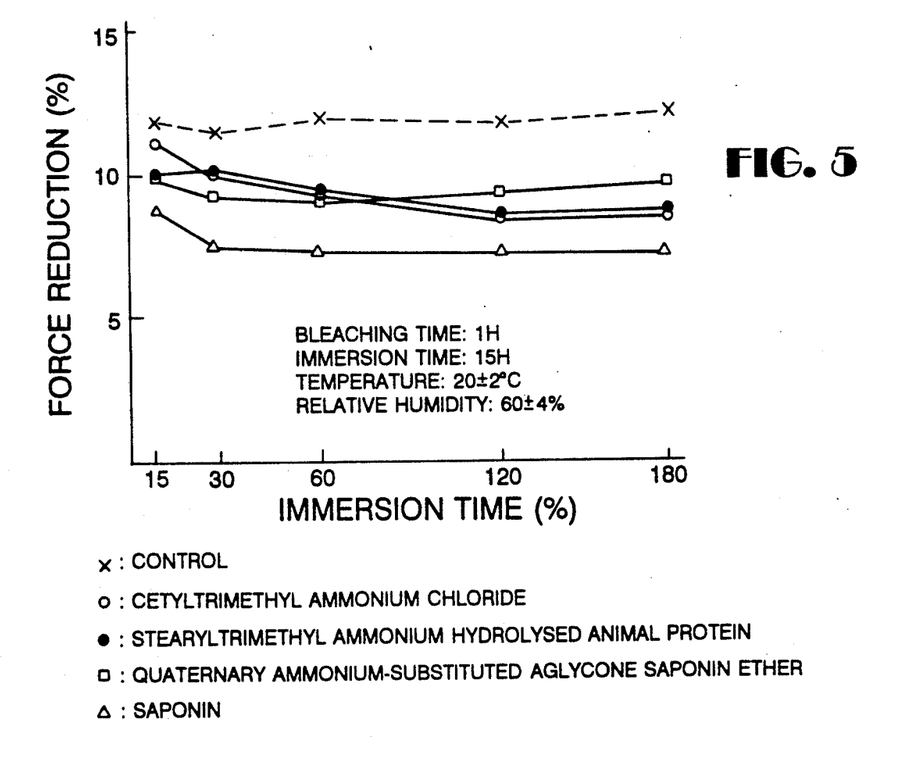

Moisture absorption regain (%) isotherms for the virgin and bleached hair treated with the compound of this invention and for the commercial standards are shown in FIGS. 1 and 2, respectively. In FIG. 3, the test materials' isotherms are shown. As shown in FIG. 1, quaternary ammonium-substituted saponin ether treated hair had much higher moisture absorption regain(%) than non-treated virgin hair, and higher value than saponin treated hair. FIG. 2 shows similar results. It is noted that the effect of moisture retention of quaternary ammonium-substituted saponin ether is distinctive at high RH by more than 40%. As shown in FIG. 3, the present compound exhibited excellent moisture retention effect than others did, and the effect of ginseng saponin itself was lower than other humectants conventionally employed in cosmetics or cation surfactants.

In human hair and skin tissues is contained skin oil. Since the sebum forms thin oil film on the surface of fiber or skin and helps them retain water and maintain the amount of water required properly, it is possible for hair or skin to have moist feel always and to prevent moisture evaporation and damage thereof resulted from the flowing out of amino acids.

Experimental Example 2. Force Reduction (%)

Cholesterol, which is known as one of the intracellular lipid components of skin, hair and wool tissue [See. Textile Research Journal, Sept., 539-542(1987)], occurs in a considerable amount in the sebum of human and is essential to maintain the skin tissue dense [See. Fragrance Journal, No. 25, 16-21 (1977)].

In order to examine the effect of quaternary ammonium-substituted saponin ether of this invention which has aglycone component which is similar to cholesterol in skin and hair, force reduction (%) which indicates the effect of increasing tensile strength of hair was tested.

The force reduction (%) was measured at 20°±2° C. and 60±4% relative humidity by using Rheo Meter (model 200-2J, Fudo Kogyo Co., Japan). The bleaching and immersion time are 1 hour and 15 hours, respectively. Under the conditions of initial hair length 50 mm, the rate of extension was 5 cm/min and full scale was 200 gf.

The percentage reduction in force required to extend a fiber 20% after treatment was calculated according to the following equation:

$$\text{Force reduction }(\%) = \frac{F_0 - F_1}{F_0} \times 100$$

where $F_0$ is the initial force required to extend a fiber 20% and $F_1$ is the force required to reextend the same fiber to 20% after treatment [See. N. B. Fair and B. S. Gupta, The use of multiple test methods in the analysis of the effect of cosmetic treatment on the surface properties of human hair, XIVth IFSCC Congress, Barcelona, Vol II. pp. 1113-1124 (1986)].

Experimental Example 3. Eye irritation

In order to evaluate the safety of quaternary ammonium-substituted saponin ether in a living body, the primary eye irritation test was carried out by using a rabbit according to the Draize's procedure [J. H. Draize, "Appraisal of the safety of chemicals in food, drug and cosmetics", Association of Food and Drug officials of the U.S., Topeeka 49 (1965)].

Figure 6:
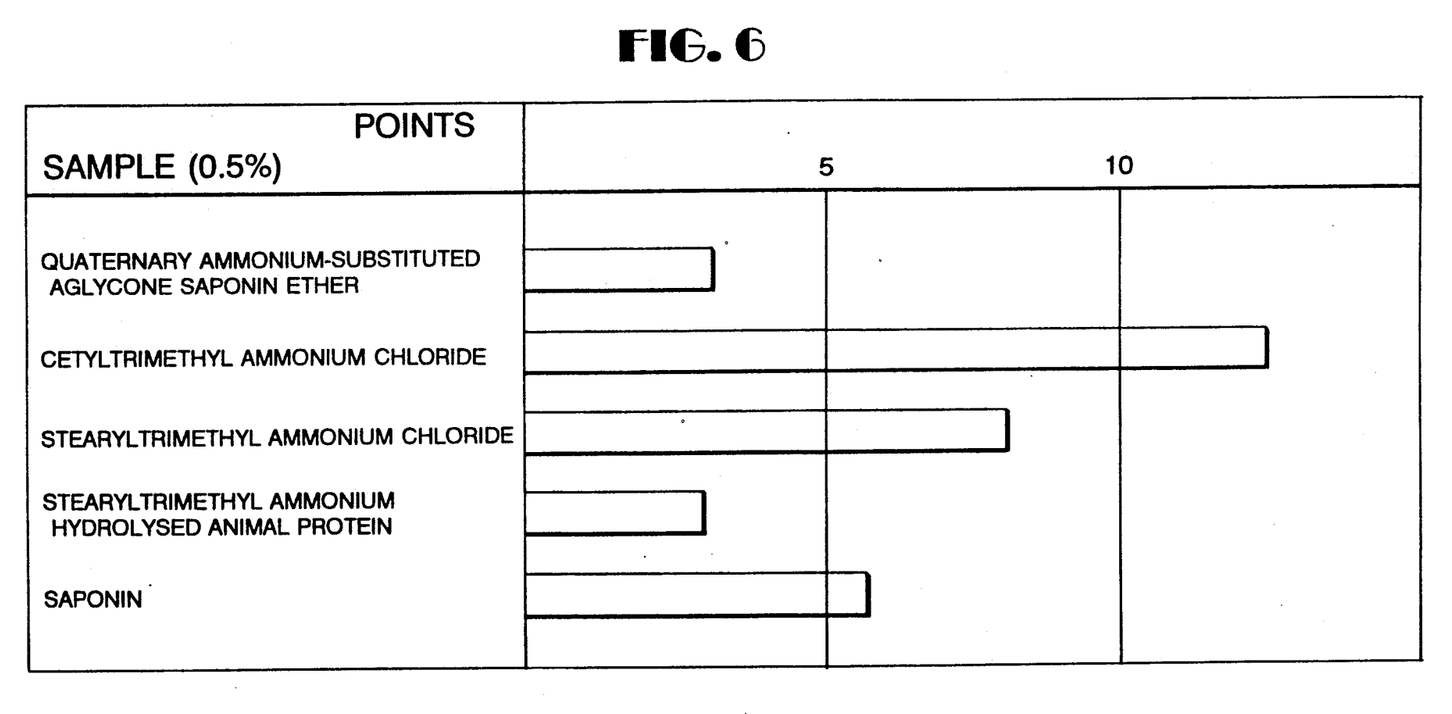
FIG. 6 shows the results of Draize eye irritation test according to Experimental Example 3.

The results are shown in FIG. 6. As shown in FIG. 6, quaternary ammonium-substituted saponin ether was less irritant than ginseng saponin as a control, and also showed less irritancy than cetyltrimethylammonium chloride and stearyltrimethyl ammonium hydrolysed animal protein which are used conventionally.

Experimental Example 4. Half-head test

The shampoo A containing the present compound and other shampoos for comparison, compositions of which are shown in Table 1, were evaluated for their conditioning effects in shampoo.

TABLE 1

| shampoo formulations | | | | | |
|---|---|---|---|---|---|
| | shampoo | | | | |
| Ingredients | A | B | C | D | E |
| Sodium lauryl ether sulfate (30%) | 40 | 40 | 40 | 40 | 40 |
| Cocoamphocarboxypropionate (70%) | 10 | 10 | 10 | 10 | 10 |
| Lauroyl myristoyl DEA | 5 | 5 | 5 | 5 | 5 |
| Quaternary ammonium-substituted ginseng aglycone saponin ether | 1.0 | — | — | — | — |

TABLE 1-continued shampoo formulations

| Ingredients | shampoo A | B | C | D | E |
|---|---|---|---|---|---|
| Ginseng saponin | — | 1.0 | — | — | — |
| Cetyltrimethylammonium chloride (25%) | — | — | 4.0 | — | — |
| Stearyltrimethylammonium hydrolysed animal protein | — | — | — | 1.0 | — |
| Propylene glycol | 3.0 | 3.0 | 3.0 | 3.0 | 3.0 |
| Methyl papaben | 0.2 | 0.2 | 0.2 | 0.2 | 0.2 |
| Perfume | q.s. | q.s. | q.s. | q.s. | q.s. |
| Citric acid (pH 6.0) | q.s. | q.s. | q.s. | q.s. | q.s. |
| Distilled water | to 100 | 100 | 100 | 100 | 100 |

The five shampoos above were prepared and the half-head test [C. Robbins "Chemical & physical behavior of human hair", Von Nostrand Reinhold, New York, 102–110 (1979)] involving 40 subjects was carried out.

All the subjects were females aged 15–40 years, and half of them had permed hair. The effects of the shampoo containing quaternary ammonium-substituted saponin ether were evaluated in regard to easiness to comb, feel of wet and dry hair as well as sheen and antistatic effects of dry hair. The hair was parted in the middle and wetted with water. To one side was applied the present compound and to the other side control shampoo for comparison. As shown in Table 2, the 40 subjects were divided into four groups by ten subjects and their hair were treated with the above five shampoos.

TABLE 2

| Group | Side of hair Left | Right |
|---|---|---|
| 1 | Shampoo A | Shampoo B |
| 2 | C | A |
| 3 | A | D |
| 4 | E | A |

For assessment of the above test items, the subject and operator choose the preferred of the two shampoos tested on the subject by evaluating the left and the right part of the subject's hair. The evaluation of the wet hair was carried out twice. Then, the hair was dried thoroughly and evaluated for the same items as of the wet hair. The final decision of the effects of dry hair was made after checking both state just after drying and 24 hours later. For each effect, 1 point was given for the chosen shampoo and 0 for the other by each subject. Also, the operator gave the points as above again for the two shampoos used for evaluation. The results of half-head tests are shown in Table 3.

TABLE 3

| Group | 1 | | 2 | | 3 | | 4 | |
|---|---|---|---|---|---|---|---|---|
| side of hair | Left | Right | L | R | L | R | L | R |
| Shampoo | A | B | C | A | A | D | E | A |
| Wet Feel | 12 | 8 | 8 | 12 | 10 | 10 | 9 | 11 |
| hair Easiness to comb | 11 | 9 | 9 | 11 | 13 | 7 | 4 | 16 |
| Dry Feel | 10 | 10 | 7 | 13 | 14 | 6 | 3 | 17 |
| hair Easiness to comb | 12 | 8 | 7 | 13 | 13 | 7 | 4 | 16 |
| Sheen | 11 | 9 | 9 | 11 | 15 | 5 | 2 | 18 |
| Antistatic effect | 12 | 8 | 10 | 10 | 16 | 4 | 4 | 16 |
| Wet hair Total Points | 23 | 17 | 17 | 23 | 23 | 17 | 13 | 27 |
| Dry hair Total Points | 45 | 35 | 33 | 47 | 58 | 22 | 13 | 67 |
| Total Points | 68 | 52 | 50 | 70 | 81 | 39 | 26 | 94 |

As shown in Table 3, shampoo A is the highest rated product by the subject and the operator. In washings, it gave rich and dense foam to the hair. Shampoo A gave wet hair a slightly better smooth feel than did shampoos B and C, and the effect of the hair was greatly superior when compared with that of shampoo E. Shampoo A made wet hair much easier to comb that did shampoo D and E, shampoo A gave excellent properties in soft feel, easiness to comb, sheen and antistatic effect when dry which are requisite properties to a shampoo for the purpose of conditioning hair.

Therefore, quaternary ammonium-substituted saponin ether of this invention is useful as cosmetic raw materials for shampoo, hair rinse, hair treatment cream, face cream, skin lotion, compact powder, foundation and the like. Particularly, it exhibits excellent conditioning effects in hair care products such as shampoo, hair rinse, hair treatment cream and the like.

Preparation Example 1. Shampoo

| 1. Quaternary ammonium-substituted saponin ether (Prepared in Example 2) | 0.5 g |
|---|---|
| 2. Sodium lauryl sulphate (30%) | 40.0 g |
| 3. Cocoamphocarboxyl propionate (70%) | 10.0 g |
| 4. Lauroyl myristoyl DEA | 5.0 g |
| 5. Propylene glycol | 1.0 g |
| 6. Preservative | q.s. |
| 7. Citric acid | q.s. |
| 8. Colorant | q.s. |
| 9. Perfume | q.s. |
| 10. Purified water | to 100.0 g |

The ingredients above 1 to 6 and 10 were well mixed, the mixture was heated under agitation to 70° C., to which were added the above ingredients 7 to 9. Then, the resulting mixture was stirred and cooled to give the desired shampoo.

Preparation Example 2. Hair rinse

| 1. Quaternary ammonium-sbstituted aglycone saponin ether (Prepared in Example 1) | 0.5 g |
|---|---|
| 2. Stearconium chloride | 0.8 g |
| 3. Stearyl alcohol | 0.5 g |
| 4. Cetyl alcohol | 0.5 g |
| 5. Propylene glycol | 5.0 g |
| 6. Polyoxyethylene(2) cetyl ether | 1.0 g |
| 7. Preservative | q.s. |
| 8. Colorant | q.s. |
| 9. Perfume | q.s. |
| 10. Purified water | to 100 g |

The ingredients above 2 to 6 were well mixed, the mixture was heated under agitation to 65° C., to which were added the above ingredients 1 and 7 to 10. Then, the resulting mixture was emulsified to give the desired hair rinse.

Preparation Example 3. Skin lotion

| | |
|---|---|
| 1. Quaternary ammonium-substituted saponin ether (Prepared in Example 5) | 0.5 g |
| 2. Ethanol | 15 g |
| 3. L-serine | 0.5 g |
| 4. Propylene glycol | 1.0 g |
| 5. Polyoxyethylene oleyl ether | 1.5 g |
| 6. Preservative | q.s. |
| 7. Colorant | q.s. |
| 8. Perfume | q.s. |
| 9. Purified water | to 100 g |

The ingredients above 1 to 9 were well mixed, stirred at room temperature and filtered to give the desired skin lotion. The process for preparing quaternary ammonium-substituted saponin ether according to this invention will be described hereinafter.

EXAMPLE 1.

Into a 1.5 l reactor equipped with a stirrer, a condenser and a fractional funnel was charged 500 ml water warmed to 40° C. and 150 g of ginseng saponin was dissolved therein. 100 g of conc. $H_2SO_4$ was added dropwise with efficient stirring and allowed to stand for 1 hour at 55° C. After completion of the reaction, the reaction solution was collected at room temperature, and the resulting precipitate was filtered, washed with water five times and dissolved in chloroform. The organic layer was washed with saturated sodium bicarbonate and with water, and removed the chloroform on a rotary evaporator to give 74 g of aglycone saponin. 60 g of this aglycone saponin was suspended in 300 ml of isopropylalcohol, 86 g of 2,3-epoxypropyltrimethyl ammonium chloride (70% aqueous solution) was slowly added thereto followed by 5 ml of 45% sodium hydroxide solution. The reaction was continued for 8 hours at 55° C. The reaction solution was neutralized with the slow addition of 4 ml of acetic acid, and then concentrated on a rotary evaporator to yield an oily residue which was dissolved in an excess of isopropyl alcohol. After standing in the freezer overnight, the precipitated materials were filtered off. The filtrate was concentrated on a rotary evaporator, dissolved in 300 ml of chloroform and washed with water three times. The organic layer was dried over anhydrous $MgSO_4$ and vacuum dried under the reduced pressure to obtain pale yellow solid, mp 240°–242° C., yield 51%. The nitrogen content was measured according to Kjeldahl method and the average molecular weight was determined by the freezing point depression and nitrogen analysis.

| | |
|---|---|
| average molecular weight | 557 |
| nitrogen content | 2.4 |
| NMR(DMSO - $d_6$) δ ppm | 3.4, 1.6, 1.3, 1.1, 0.9 |

EXAMPLE 2

Into a 300 ml flask equipped with a condenser and a magnetic stirrer were charged 10 g of ginseng saponin and 80 g of water, the temperature was raised to 40° C. with stirring and 30 ml of solution of 0.03M 2,3-epoxypropyltrimethylammonium chloride (70% aqueous solution) and a small amount of sodium hydroxide was added thereto. The resulting mixture was reacted with stirring on a oil bath of 50° C. for 5 hours. The reaction solution was neutralized by slowly adding 0.21 ml of acetic acid, concentrated under reduced pressure by a rotary evaporator and dissolved thoroughly in 100 ml of isopropyl alcohol. After standing in the freezer overnight, the precipitates were filtered off. The filtrate was dried under reduced pressure to give a crude product in pale yellow solid. It was purified by chromatography on a column of Sephadex G-10 and eluted with water. The fractions containing the main product were combined and evaporated to obtain about 9.2 g of quaternary ammonium-substituted saponin ether.

EXAMPLE 3

60 g soya saponin was dissolved in 150 ml of methanol by heating to 40° C. A small amount of glucosidase was added thereto and stirring was carried out to remove the sugar moieties from the soya saponin. An aqueous solution of 0.3M 2,3-epoxypropyltrimethyl ammonium chloride in 200 ml water containing a small amount of sodium hydroxide was added thereto and the reaction was continued with stirring at 50° C. for 3 hours. After completion of the reaction, the reaction solution was neutralized with 15 ml of acetic acid. Then, the same procedure as Example 1 was followed to obtain about 58 g of the desired product.

EXAMPLE 4

Into a 1 l reactor equipped with a stirrer, a condenser and a fractional funnel were charged 30 g of ginseng saponin and 500 ml of water and the mixture was stirred for about 30 min, after which 30 ml of 5% hydrochloric acid was added. The temperature of the reactor was raised to 55° C. and maintain the same temperature for 1 hour. The resulting precipitated materials were filtered, and the filtrate was washed with water several times until it reaches a neutral pH. The filtrate without drying was placed into a 1 l reactor, 50 ml of isopropyl alcohol was added thereto and the stirring was carried out, after which a small amount of sodium hydroxide was added thereto. The stirring was continued for further 30 min, 40 ml of ethylene oxide was added, the temperature of the reactor was raised to 50° C. and maintained this temperature for 2 hours. Then, 45 ml of aqueous solution of 0.08M 3-chloro-2-hydroxypropyl-trimethyl ammonium chloride was added, the resulting reaction mixture was maintained at 50° C. for two hours and heated to 70° C. which was maintained for about 15 min. After completion of the reaction, the reaction mixture was neutralized with 6 ml of acetic acid. Then, the same procedure as Example 1 was followed to obtain about 17 g of the desired product.

EXAMPLE 5

10 g crude ginseng saponin was partitioned onto a mixture of n-butanol and water (1:1) and the n-butanol layer was evaporated under reduced pressure to give a residue, which was dissolved in a small amount of solution of methanol-water. The precipitate obtained by the addition of excess ether was repartitioned onto n-butanol-water (1:1) and the n-butanol layer was vacuum dried by a rotary evaporator to give 6 g of the purified saponin. This product was placed into a 300 ml reactor, 60 ml of isopropyl alcohol was added thereto and the mixture was stirred for 15 min followed by raising the temperature to 40° C. slowly. About 10 g of 2,3-epoxypropyltrimethylammonium chloride solution (70% aqueous solution) was added followed by 0.6 ml of sodium hydroxide (45%), and the stirring was carried out at 45° C. for 21 hours. After completion of the reaction, the pH of the solution was adjusted to 7.0 by adding slowly 0.03M H$_2$SO$_4$. Then, the solution was concentrated on a rotary evaporator, an excess isopropyl alcohol was added and the mixture was allowed to stand to give a precipitate. Thus obtained precipitate was filtered off. The filtrate was evaporated under reduced pressure, dissolved in the minimum amount of distilled water and purified by gel chromatography on Sephadex G-10 column and eluted with distilled water. The fractions containing main product were combined and freeze-dried to give about 7.5 g of quaternary ammonium-substituted saponin ether.

EXAMPLE 6

6 g Aglycone saponin prepared according to the procedure of Example 1 was dissolved in 35 ml of isopropyl alcohol, 17.5 g of 2,3-epoxypropyldimethyldodecyl ammonium chloride solution (60% aqueous solution) was added thereto gradually and the temperature was raised to 41° C. After adding 0.6 ml 45% sodium hydroxide solution dropwise slowly, the reaction was continued for 12 hours at 58° C. After completion of the reaction, the solution was adjusted to pH 7.0 by adding slowly 0.03M hydrochloric acid and evaporated on a rotary evaporator. The precipiated materials produced by adding excess isopropyl alcohol were filtered off. The filtrate was evaporated on a rotary evaporator and dissolved in a minimum amount of methanol, which is purified by gel chromatography on Sephadex LH-20 column and eluted by methanol. The fractions containing the purified product were combined and evaporated on a rotary evaporator to give about 6.9 g of the desired product.

EXAMPLE 7

6 g Aglycone sapogenin prepared according to the procedure of Example 1 was dissolved in 30 ml of isopropyl alcohol, 13 g of 2,3-epoxypropyldimethyl cyclohexylamine chloride solution (69% aqueous solution) was added gradually thereto and 0.6 ml of 45% sodium hydroxide solution was added dropwise under stirring. The reaction temperature was raised to 55° C. at which the reaction was continued for 12 hours. The reaction mixture was neutralized with 0.01M H$_2$SO$_4$, evaporated on a vacuum rotary evaporator and an excess isopropyl alcohol was added thereto. The resulting mixture was allowed to stand to yield a precipitate, which was filtered off. Then, the same procedure as Example 1 was followed to obtain about 6.4 g of the desired product.

EXAMPLE 8

6g Aglycone sapogenin prepared according to the procedure of Example 1 was dissolved in 40 ml of isopropylalcohol, 22.4 g of 2,3-epoxypropyldimethyloleyl ammonium chloride solution (67% aqueous solution) was added gradually with stirring and the temperature was raised to 45° C. 0.8 ml of 45% sodium hydroxide solution was added slowly and the reaction was continued at 55° C. for 15 hours. When the reaction was completed, the solution was adjusted to pH 6.8 with acetic acid. The solution was concentrated to a total volume of about 30 ml by a vacuum rotary evaporator and an excess isopropyl alcohol was added thereto. The resulting mixture was allowed to stand to yield a precipitate, which was filtered off and the filtrate was dried by a vacuum rotary evaporator to give a solid. Thus obtained solid was well pulverized and washed with water with a continuous pulverization until it reaches a neutral pH, and then vacuum dried to give about 7.1 g of a solid product.

EXAMPLE 9

6 g Soya saponin was dissolved in 30 ml of methanol by heating to 40° C. and a small amount of glucosidase was added thereto. The resulting mixture was stirred for 1 hour and allowed to stand for 3-4 hours. The precipitate was filtered off and methanol was removed by a vacuum rotary evaporator to give a solid product. This product was dissolved in 30 ml of chloroform and 30 ml of water added thereto to carry out partition. Chloroform was removed under reduced pressure to obtain about 3.2 g of a solid product. To this solid, was added 20 ml of isopropyl alcohol followed by 9.2 g of 2,3-epoxypropyldimethyldodecyl ammonium chloride (68% aqueous solution) with stirring, the temperature was raised to 40° C. and 0.3 ml of 45% sodium hydroxide was added dropwise. The temperature was raised to 58° C. and the stirring was continued at the same temperature for 12 hours. Then, the same procedure as Example 6 was followed to give about 3.2 g of dimethyldodecyl ammonium-substituted aglycone soya saponin ether.

EXAMPLE 10

Into a 200 ml flask, was placed 6 g of soya saponin and 50 ml of isopropyl alcohol, and the temperature was raised gradually to 40° C. with stirring. About 5.5 g of 2,3-epoxypropyldimethylethyl ammonium chloride solution (70% aqueous solution) was added thereto, followed by the addition of 0.35 ml of sodium hydroxide solution(45%). The temperature was raised to 50° C., and the reaction solution was stirred for 15 hours and neutralized with 0.03M hydrochloric acid. Then, the same procedure as Example 5 was followed to give about 3.5 g of dimethylethyl ammonium-substituted soya saponin ether.

EXAMPLE 11

Into 20 ml of isopropyl alcohol was added gradually 10 g of crude saponin with stirring and 0.02 ml of 45% sodium hydroxide was introduced. The temperature was raised to 30° C. and 20 g of 2,3-epoxypropyltrimethylammonium chloride solution(70%) was added dropwise. The temperature was raised to 55° C. and the reaction was continued for 6 hours. After completion of the reaction, the reaction solution was cooled to room temperature, 0.07 ml of acetic acid was added and the resulting solution was allowed to stand for 30 min. To the neutralized solution was added dropwise slowly 300 ml of isopropyl alcohol with stirring to yield a jelly precipitate. The supernatant was removed by decantation and the residue was dried under reduced pressure. Then, gel chromatography using Sephadex G-10 column was carried out by the same procedure as Example 5 to give about 5.8 g of trimethyl ammonium-substituted ginseng saponin ether.

While the invention has been described in its preferred forms by way of Example, it should be understood that the description is for illustrative purpose only, and that changes and modifications may be made by those who skilled in the art without departing from the purpose and spirit of the following claims.

What is claimed is:

1. A quaternary ammonium-substituted saponin ether of the following formula (I):

R—O—Rsap—O—R'              (I)

wherein, —O—Rsap—O— represents a saponin or an aglycone saponin which is a polycyclic compound of saponin selected from the group consisting of a soya saponin of the formula (IV):

wherein both of $R_4$ and $R_5$ are a glucose moiety, or $R_4$ is a glucose moiety and $R_5$ is hydrogen atom; ginseng saponins of the formulae (Va) and (Vb):

wherein, $R_4$ and $R_5$ are a glucose moiety; and aglycones thereof produced by removing the sugar moieties $R_4$ and $R_5$ from the saponins of formula (IV), (Va) or (Vb) and R and R' are hydrogen or a quaternary ammonium-containing substituent attached to the aglycone saponin or saponin and at least one of them is a quaternary ammonium-containing substituent of the following formula:

wherein, $(Q)^-$ is an anion of strong inorganic acid; $R_1$ is methyl; $R_2$ and $R_3$ are the same or different from each other and are each alkyl or an olefin group containing 18 or less carbon atoms; and t is the valency of the group Q, when prepared by reacting a saponin or aglycone saponin with a quaternary ammonium halohydrin of the following formula (II):

wherein, Hal is a leaving group; and $(Q)^-$, $R_1$, $R_2$, $R_3$ and t have the same meanings as above.

2. The quaternary ammonium-substituted saponin ether according to claim 1, wherein in the definition of $(Q)^-$ said anion of said strong inorganic acid is chloride, bromide or iodide.

3. A quaternary ammonium-substituted saponin ether of the following formula (I):

R—O—Rsap—O—R'             (I)

wherein,
—O— Rsap—O— represents a saponin or an aglycone saponin which is a polycyclic compound of saponin selected from the group consisting of a soya saponin of the formula (IV):

wherein, both of $R_4$ and $R_5$ are a glucose moiety, or $R_4$ is a glucose moiety and $R_5$ is a hydrogen atom; ginseng saponins of the formulae (Va) and (Vb):

wherein, $R_4$ and $R_5$ are a glucose moiety; and aglycones thereof produced by removing the sugar moieties $R_4$ and $R_5$ from the saponins of formula (IV), (Va) or (Vb); and R and R' are hydrogen or a quaternary ammonium-containing substituent attached to the aglycone saponin or saponin and at least one of them is a quaternary ammonium-containing substituent of the following formula:

wherein, $(Q)^-$ is an anion of strong inorganic acid; $R_1$ is methyl; $R_2$ and $R_3$ are the same or different from each other and are each alkyl or an olefin group containing 18 or less carbon atoms; and t is the valency of the group Q, when prepared by reacting a saponin or aglycone saponin with a quaternary ammonium epoxide of the following formula (III):

wherein, $R_1$, $R_2$, $R_3$ $(Q)^-$ and t have the same meanings as above.

4. The quaternary ammonium-substituted saponin ether according to claim 3, wherein in the definition of $(Q)^-$ said anion of said strong inorganic acid is chloride, bromide or iodide.

5. The quaternary ammonium-substituted saponin ether according to claim 1, wherein about 1 to 4 moles of the quaternary ammonium salt is employed relative to one mole of the saponin or aglycone saponin.

6. The quaternary ammonium-substituted saponin ether according to claim 1, wherein the substitution reaction is carried out in a solvent selected from the group consisting of isopropyl alcohol and a mixture of water and isopropyl alcohol.

* * * * *